United States Patent [19]
Solheim et al.

[11] Patent Number: 5,526,676
[45] Date of Patent: Jun. 18, 1996

[54] PROFILING OF SELECTED ATMOSPHERIC CHARACTERISTICS UTILIZING PASSIVE MICROWAVE REMOTE SENSING

[75] Inventors: Fredrick S. Solheim, Boulder; Lee A. Erb, Longmont; Loren D. Nelson, Evergreen; Randolph H. Ware, Boulder, all of Colo.

[73] Assignee: Radiometrics Corporation, Boulder, Colo.

[21] Appl. No.: 385,140

[22] Filed: Feb. 7, 1995

Related U.S. Application Data

[63] Continuation-in-part of Ser. No. 196,943, Feb. 14, 1994, abandoned.

[51] Int. Cl.$^6$ ..................................................... G01W 1/00
[52] U.S. Cl. ..................... 73/29.01; 73/170.27; 374/122; 324/640
[58] Field of Search ........................... 73/29.01, 170.27; 374/122; 324/640

[56] References Cited

U.S. PATENT DOCUMENTS

| | | |
|---|---|---|
| 3,359,557 | 12/1967 | Fow . |
| 3,380,055 | 4/1968 | Fow . |
| 3,465,339 | 9/1969 | Marner . |
| 3,911,435 | 10/1975 | Mardon et al. . |
| 4,178,100 | 12/1979 | Levis . |
| 4,282,525 | 8/1981 | Gustincic et al. . |
| 4,385,516 | 5/1983 | Uffelman . |
| 4,493,553 | 1/1985 | Korb et at. . |
| 4,873,481 | 10/1989 | Nelson ...................................... 324/640 |
| 5,065,615 | 11/1991 | Hill ........................................ 324/640 |
| 5,149,198 | 9/1992 | Sterzer . |
| 5,176,461 | 1/1993 | Chive Maurice et al. . |
| 5,218,357 | 6/1993 | Sukamoto et al. . |

OTHER PUBLICATIONS

Gloersen: "The SEASAT–A Scanning Muiltidiamid UW Radiometer" OCEANS '76 Conference–Sep. 1976–USA.

"Experimental Determination of Temperature Profiles by Ground–Based Microwave Radiometry", E. R. Westwater, J. B. Snider and A. V. Carlson, Jun. 1975, (Journal of Applied Meterology, vol. 14, No. 4).

"Remote Sensing of Atmospheric Water Vapor by Ground–Based Microwave Radiometery", E. R. Westwater, M. J. Falls, and M. T. Decker, Apr. 1985, (Proceedings of the 1985 International Symposium on Moisture and Humidity, Washington, D.C.).

"A Review of Ground–Based Remote Sensing of Temperature and Moisture by Passive Microwave Radiometers", Jan. I. H. Askne and Ed R. Westwater, May 1986, IEEE Transations on Geoscience and Remote Sensing, vol. GE–24, No. 3.

"Ground–Based Passive Probing Using the Microwave Spectrum of Oxygen", E. R. Westwater, Sept. 1965, (RADIO SCIENCE Journal of Research NBS/USN-C–URSI), vol. 69D, No. 9.

"Atmospheric Profiling of Water Vapor Density with A 20.5–23.5 GHz Autocorrelation Radiometer", Christopher S. Ruf and Calvin T. Swift, Aug. 1988, (Journal of Atmospheric and Oceanic Technology, vol. 5, No. 4.

*Primary Examiner*—Kenneth A. Wieder
*Assistant Examiner*—Jose M. Solis
*Attorney, Agent, or Firm*—Harold A. Burdick

[57] ABSTRACT

Apparatus and methods for profiling atmospheric temperature, water vapor and/or cloud liquid content utilizing passive microwave remote sensing are disclosed. The apparatus includes an antenna for receiving atmospheric microwave emissions having frequencies of interest, a highly stable, tunable frequency synthesizer, and downconverting system receiving selected frequency outputs from the synthesizer and the received emissions and, responsive thereto, providing output signals indicative of the frequencies of interest and representing the profile.

26 Claims, 7 Drawing Sheets

OTHER PUBLICATIONS

"An Automatic Profiler of the Temperture, Wind and Humidity in the Troposphere", D. C. Hogg, M. T. Decker, F.O. Guiraud, K. B. Earnshaw, D. A. Merritt, K. P. Moran, W. B. Sweezy, R. G. Strauch, E. R. Westwater and C. G. Litttle, (Journal of Applied Meterology, vol. 22, No. 5.), May 1983.

"Profiling Atmospheric Water Vapor by Microwave Radiometry", J. R. Wang, J. L. King, T. T. Wilheit and G. Szejwach, L. H. Gesell, R. A. Nieman, D. S. Niver, B. M. Krupp, J. A. Gagliano, May, 1983, (American Meteorological Society, Journal of Climate and Applied Meteorology, vol. 22)

"Statistical Retrieval of Temperature Profiles From Ground Based Measurements", Edward M. Measure, T. L. Barber, Young P. Yee, Dick R. Larson, Nov. 1990, (Business Advancement Center).

"Atmospheric Water–Vapor Profiling by Ground–Based Radiometry at 22 and 183 GHz", Jan I. H. Askne, and B. Goran Skoog, Jul. 1983, (IEEE Transactions on Geoscience and Remote Sensing, vol. GE–21, No. 3.

"Experimental Evaluation of Ground–Based Microwave Radiometric Sensing of Atmospheric Temperature and Water Vapor Profiles", M. T. Decker, E. R. Westwater and F. O. Guiraud, Dec. 1978, (Journal of Applied Meteorology, vol. 17.

"Measurements of the Cosmic Background Radiation Temperature at 3.3 and 9.1 mm" Giovanni DeAmici, Chris Witebsky, George F. Smoot, and Scott D. Friedman, Jun,. 15, 1984, (Physical Review D–Particles and Fields, vol. 29, No. 12).

"Noise Calibration Repeatability of an Airborne Third–Generation Radiometer" Hans–Juergen C. Blume, Apr., 1977, NASA Langley Research Center, Hampton, VA).

"Low–Frequency Measurement of the Spectrum of the Cosmic Background Radiation", George F. Smoot, Giovanni De Amici, Scott D. Friedman, and Chris Witebsky, and Nazzareno Mandolesi, R. Bruce Partridge, Giorgio Sironi, and Luigi Danesa and Gianfranco DeZotti, Sep. 19, 1983, (Physical Review Letters, vol. 51, No. 12).

"Measurement of the Cosmic Background Radiation Temperature at 6.3 cm", N.Mandolesi, P. Calzolari, S. Cortiglioni, and G. Morigi, Jun. 15, 1984, (Physical Review D, vol. 29, No. 12).

"Precision Temperature Reference for Microwave Radiometry", Walter N. Hardy, Mar. 1972, (IEEE Transactions on Microwave Theory and Techniques).

PROFILING OF SELECTED ATMOSPHERIC CHARACTERISTICS UTILIZING PASSIVE MICROWAVE REMOTE SENSING

GOVERNMENT SUPPORT

This invention was made with Government support under contract awarded by the Department of Defense. The Government has certain rights in the invention.

RELATED APPLICATION

This Application is a Continuation In Part of U.S. patent application Ser. No. 08/196,943 filed Feb. 14, 1994 (now abandoned) and entitled PROFILING OF SELECTED ATMOSPHERIC CHARACTERISTICS UTILIZING PASSIVE MICROWAVE REMOTE SENSING by Frederick S. Solheim.

FIELD OF THE INVENTION

This invention relates to radiometers which utilize passive microwave remote sensing techniques, and, more particularly, relates to such radiometers utilized for profiling atmospheric characteristics.

BACKGROUND OF THE INVENTION

Atmospheric temperature profiling microwave radiometers heretofore known and/or utilized have employed a plurality of discrete Gunn diode oscillators for the local oscillator. In such cases the number of frequencies of which the radiometer receiver is capable, and the frequencies themselves, are fixed.

Moreover, Gunn oscillators have several characteristics related to frequency stability that are undesirable for use in observations between 50 and 60 GHz. Gunn oscillators have a poor frequency stability with physical temperature changes, up to two MHz/°C. If Gunn oscillators are allowed to be at ambient temperature, this equates to as much as a 140 MHz shift over a −20° C. to +50° C. operating range. This results in less than desirable temperature profiling. Therefore, current uses of Gunn oscillators in such systems require careful temperature stabilization of the oscillator housing. As a consequence, these instruments are complex, unwieldy, and power consumptive. Additionally, warm-up times are significantly long. Even when temperature stabilized, Gunn oscillators will wander over many megahertz in frequency. This wandering has a grave effect upon the accuracy of temperature profiling. Further improvement could thus be utilized.

Now known methods of atmospheric water vapor profiling are dramatically effected by various weather conditions, some methods being ineffective in the presence of clouds. Many current techniques for profiling water vapor are not passive (for example, radiosonde and/or laser techniques) thereby introducing complexity and added expense to such measurements. New approached to such profiling could thus be utilized.

Radiometers are calibrated by establishing the gain and offset of the system. Offsets can be quite high, more than 700K, depending upon the receiver dark noise. The sky observables in any waveband have a range of less than 100K. Therefore, a small percentage change in receiver noise can induce a significant error in observables. Receiver stability, or frequent gain/offset evaluations of the receiver, are therefore necessary.

Most radiometer systems incorporate internal references in the form of hot and cold loads, targets of known temperature, and/or known noise sources. These references are used as absolute or as transfer calibration (near-term calibration) standards. Hot and cold loads are an incomplete calibration in that they do not include front end components of the radiometer such as the antenna system, dielectric window, and antenna isolators. Also, hot loads require an extrapolation of calibration data since hot loads are above ambient temperature and sky observables are at ambient temperature or below. It would be beneficial for calibration temperatures to span the range of observables. An improved calibration system for these types of systems could thus be utilized.

While under proper conditions and in selected wavebands, data from "tipping curves" are quite resolute, absolute calibration of radiometers in the 20 to 35 GHz range can only be accomplished with "tipping curves" when the atmosphere is transparent enough (opacity is low enough) such that there is a significant change in sky brightness with zenith angle, and provided that the sky can be assumed horizontally stratified and uniform. If not, it has been found that up to 15% variations in brightness in these wave-bands will occur, resulting in erroneous calibration values. Further improvement in calibration is therefore required.

SUMMARY OF THE INVENTION

This invention provides an atmospheric temperature and/or water vapor profiling apparatus and method, the apparatus including, or being utilized with, a device having an antenna for receiving atmospheric microwave emissions having frequencies of interest, and including a frequency synthesizer providing a plurality of selected frequency outputs and downconverting system receiving the selected frequency outputs and the received emissions and, responsive thereto, providing output signals indicative of the frequencies of interest and representing the profile of the atmospheric characteristic.

For use as an atmospheric temperature profiler, the frequencies of interest are a broad atmospheric oxygen line assemblage in a waveband preferably between about 40 and 80 GHz, and the frequency synthesizer is tunable across this waveband. The selected frequency outputs may be any of a plurality of (for example, about 16) frequency intervals between 40 and 80 GHz. The oxygen resonance line at 119 GHz may also be tuned across from about 110 to 125 Ghz.

For use as an atmospheric water vapor profiler, the frequencies of interest are a pressure broadened water vapor line in a selected waveband, and the frequency synthesizer is tunable across this waveband to provide output signals representing a profile of atmospheric water vapor. The pressure broadened water vapor line waveband is preferably in the range of about 16 to 28 GHz. In addition, in such configuration, received frequencies of interest may also include a frequency in the range of 30 to 36 GHz, the apparatus being further provided with means for resolving emissions in the 30 to 36 GHz range thus providing an output signal indicative of liquid content of the atmosphere. The pressure broadened waveband between 175 and 190 GHz is also usable, especially for "top down" (e.g. satellite or aircraft) observations. The liquid content of the atmosphere may be determined in such applications by observing in the region of 80–90 GHz and in the region of 150–160 GHz.

For use as an atmospheric cloud liquid water profiler, the frequencies of interest are due to the broad oxygen line assemblage in the waveband between about 40 and 80 GHz, and the frequency synthesizer is tuneable across this waveband. Observations are made on both the high frequency and the low frequency side of the oxygen line to determine the asymmetric and height dependent contribution due to cloud liquid.

The frequency synthesizer includes a tunable oscillator connected to a frequency controller referenced to a stable frequency reference. A processor controls tuning of the frequency synthesizer to each of an ensemble of user defined frequencies. Means for characterizing gain and offset of the apparatus at each observation to enhance accuracy of the profile is provided.

The method of this invention includes admitting atmospheric microwave emissions containing frequencies of interest into a volume, synthesizing a plurality of signals responsive to the atmospheric microwave emissions at the frequencies of interest and admitting the signals into the volume to downconvert the emissions at the frequencies of interest, and generating output signals indicative of the atmospheric microwave energy at the frequencies of interest to provide a profile of the atmospheric characteristic.

It is therefore an object of this invention to provide an improved apparatus and method for providing a profile of a selected atmospheric characteristic.

It is another object of this invention to provide improved atmospheric temperature profiling.

It is another object of this invention to provide for atmospheric water vapor or cloud liquid water profiling.

It is still another object of this invention to provide an atmospheric temperature and/or water vapor profiling apparatus used with an antenna for receiving atmospheric microwave emissions containing frequencies of interest and including a frequency synthesizer providing a plurality of selected frequency outputs and downconverting system receiving the selected frequency outputs and the received emissions and, responsive thereto, providing output signals indicative of the microwave energy emitted at the frequencies of interest and representing the profile.

It is yet another object of this invention to provide a passive microwave radiometer for determining a profile of a selected atmospheric characteristic including an antenna for receiving atmospheric microwave emissions containing frequencies of interest, a frequency synthesizer tunable across a plurality of user selected frequency intervals that are responsive to the atmospheric microwave emissions at the frequencies of interest, and means connected with the antenna and the frequency synthesizer for generating output signals indicative of the atmospheric emissions at the frequencies of interest responsive to receipt of the emissions and tuning of the frequency synthesizer across the intervals to provide the profile.

It is still another object of this invention to provide a method for profiling atmospheric characteristics of interest including the steps of admitting atmospheric microwave emissions having frequencies of interest into a volume, synthesizing a plurality of signals responsive to the atmospheric microwave emissions at the frequencies of interest and admitting the signals into the volume to downconvert the emissions at the frequencies of interest, and generating output signals indicative of the atmospheric microwave energy emitted at the frequencies of interest to provide a profile of an atmospheric characteristic.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 2:
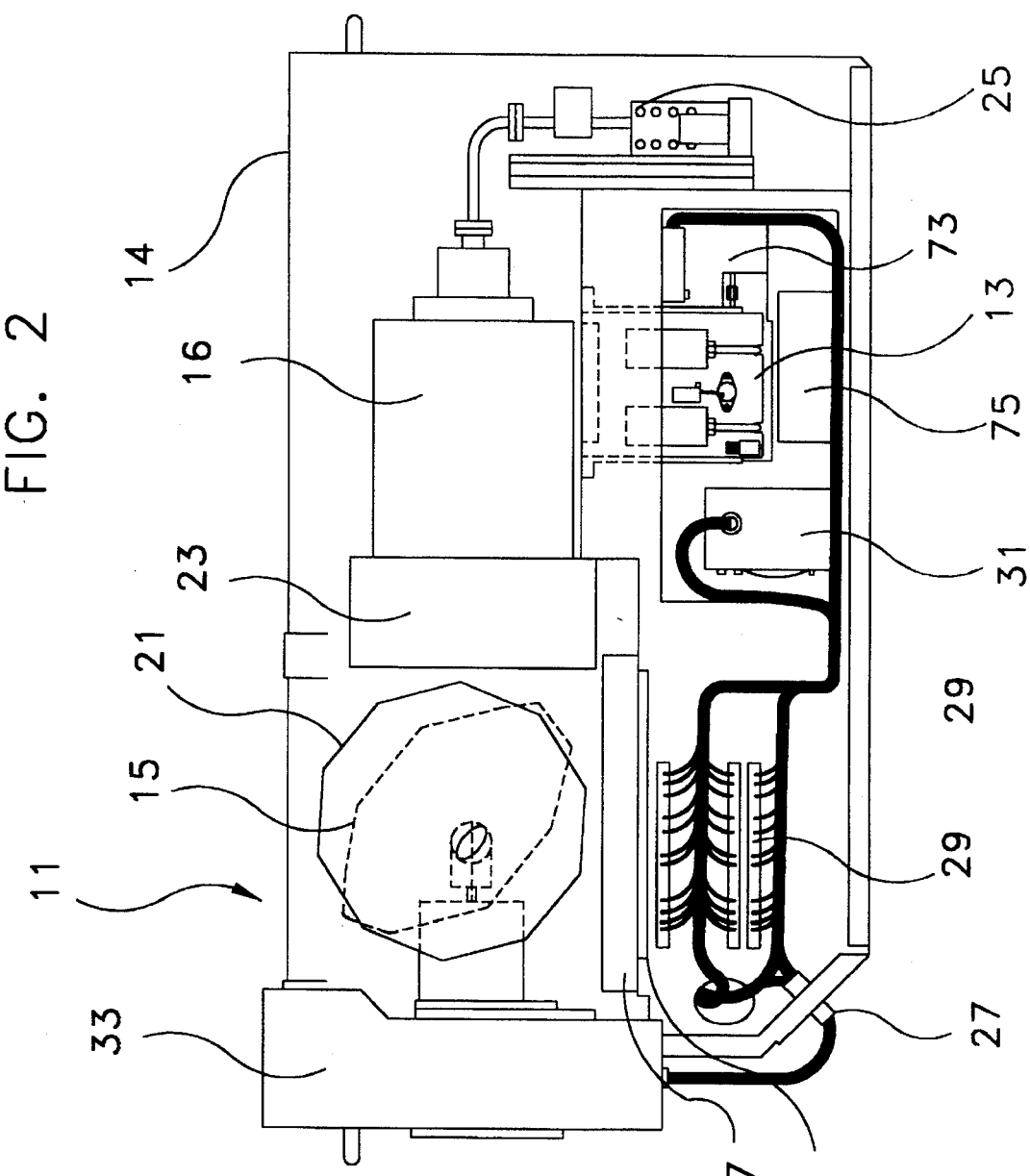
FIG. 2 is a sectional view taken through section lines 2—2 of FIG. 1.
Figure 1:
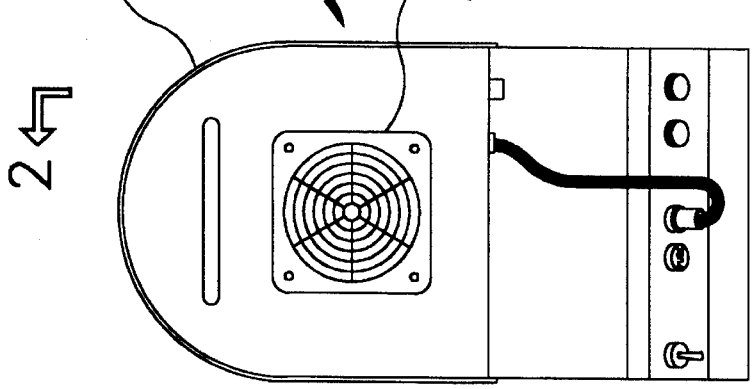
FIG. 1 is an end view of the profiling apparatus of this invention.

An illustration of an existing water vapor radiometer 11, as also illustrated and disclosed in detail in U.S. Pat. No. 4,873,481 (which U.S. Patent is incorporated hereinto in its entirety by this reference, integrated with the profiling apparatus 13 of this invention is shown in FIGS. 1 and 2.

Apparatus 13 is a microwave receiver system, also called a radiometer, that can determine the profile of the physical temperature of the atmosphere over a plurality of selected altitudes and/or the profile of water vapor of the troposphere to a high degree of accuracy. The profile measurements are accomplished by a series of observations of the sky at different frequencies.

The radiometer is mounted in housing 14 and includes steerable elevation mirror 15 that can point to all elevation angles. When pointed downward, the field of view of antenna 16 is filled with black body 17 of a known temperature as determined and updated by reference to temperature sensor 19. Observing black body 17 establishes the receiver offset. When pointed upward, through window 21, atmospheric emissions having frequencies of interest are received and observed.

Radiometer 11 includes side lobe collar 23 to negate the effects of antenna side lobes of dual feed Gaussian optical antenna 16. Existing water vapor microwave receiver 25 is provided, as are standard PC and power connectors 27, card cage 29 and power supply 31. Dew blower 33 is provided to assure field efficacy of dielectric window 21.

Figure 3:
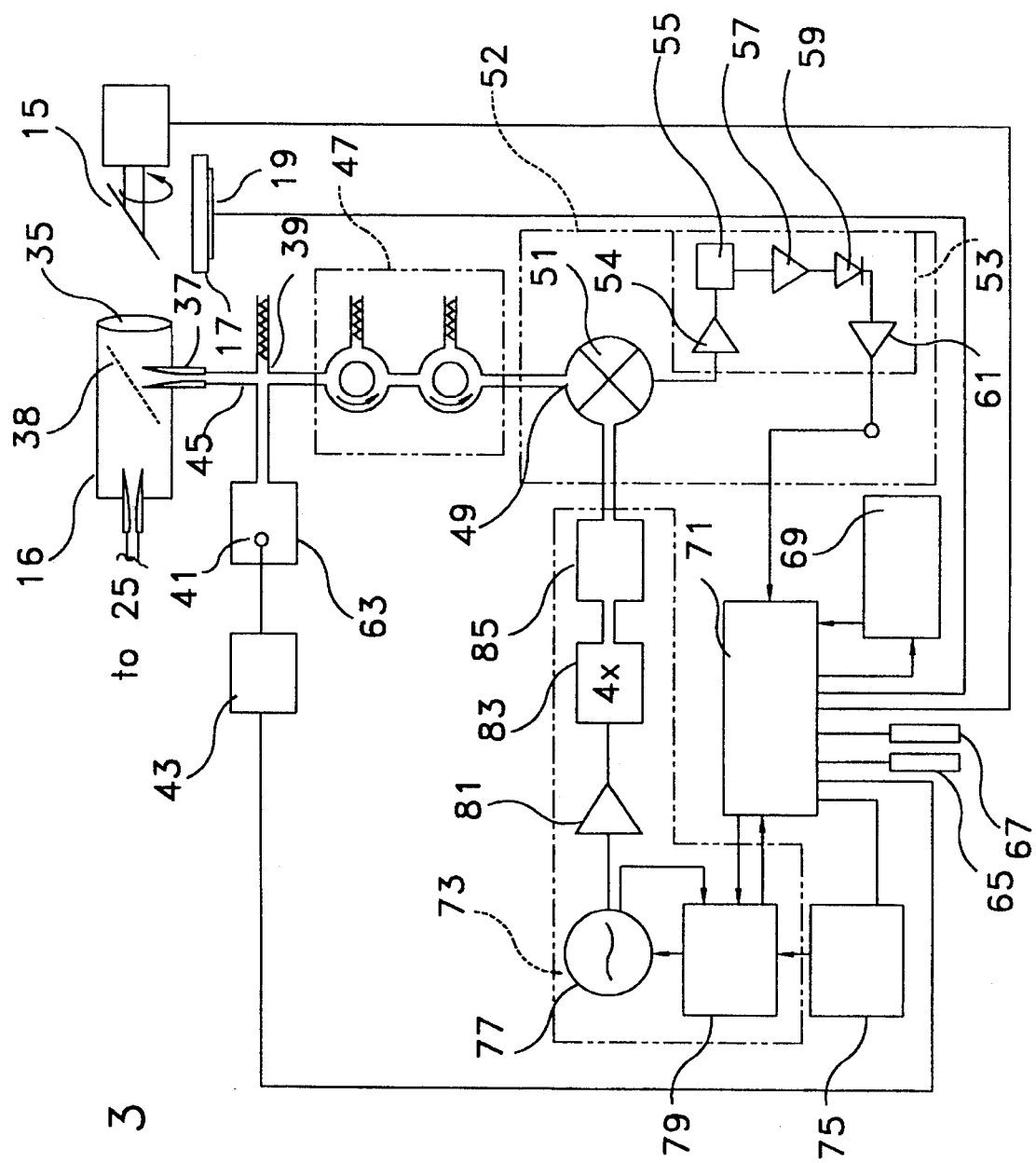
FIG. 3 is a diagrammatic illustration of the temperature profiling apparatus in accord with this invention.

A shown in FIG. 3, antenna 16, having lens 35 thereat, includes corrugated feed horn 37 receiving microwave emissions, and thus the frequencies of interest, as focussed by lens 35. Antenna 16, where multiple receivers are used, may include signal splitter 38. A wire grid polarizer is preferable for this application. This grid consists of a plane of thin parallel conductors within the focused sky signal beam. The grid passes one polarization of the incoming beam, and reflects the other. The passed polarization may be utilized, for example, for any existing receiver operations, such as water vapor receiver 25, while the other polarization is reflected 90°, by placing the grid at 45° to the axis of the beam, and thus focused into corrugated feed horn 37. This grid polarizer offers beam splitting without suffering any signal loss.

Directional coupler 39 injects signal of known equivalent temperature from stabilized noise diode 41 connected with driver 43 into antenna waveguide 45 when the noise diode is on. Measuring the contribution of the injected signal to the receiver output establishes the gain of the receiver. The passive radiometer can be constructed with waveguide of predetermined size, or can be constructed utilizing microstrip, stripline, or monolithic microwave integrated circuits (MMIC) methods.

Coupler 39 is followed by isolator 47 (preferably having a band width of about 6 GHz) to prevent local oscillator leakage from RF port 49 of mixer 51 from exiting and re-entering antenna 16 as an error source. Downconversion system 52, including biased mixer 51, is followed by signal conditioning system 53 having amplification stage 54, IF filtering stage 55, further amplification stage 57, detection by square law detector 59, and current amplification stage 61.

The accuracy of the radiometer receiver, and therefore the profile of temperature or of water vapor, is dependent upon the stability and resolving power of the receiver, and of the stability of the noise diode gain reference. To increase the stability of noise diode 41, its mount 63 is held at a constant temperature. Further, when noise diode 41 is not reverse voltage biased for signal output, a forward current is run through the noise diode to keep its internal temperature high and reduce its settling time when switched to reverse bias.

Ambient surface temperature and barometric pressure sensors 65 and 67 are provided to enhance profiling when properly modeled into profile inversion software.

The operation of the radiometer antenna system, including signal splitter 38, the noise diode injection method, filtering, amplification, and detection of the IF signal, and data reduction methods are described in incorporated U.S. Pat. No. 4,873,481.

The radiometer is controlled with high level commands from computer 69 running, for example, a FORTRAN program. All data is logged onto the PC hard disk, and reduced data are displayed to the PC screen. The FORTRAN program conveys simple commands, for example via RS232 protocol, to onboard microprocessor 71 (for example, a Motorola 68HC11 microprocessor) that translates these commands to low level control of the various radiometer systems. Microprocessor 71 controls the pointing of antenna mirror 15, turns on and off the various oscillators and noise diode 41, monitors temperatures and pressures, and measures system and reference voltages.

Figure 4:
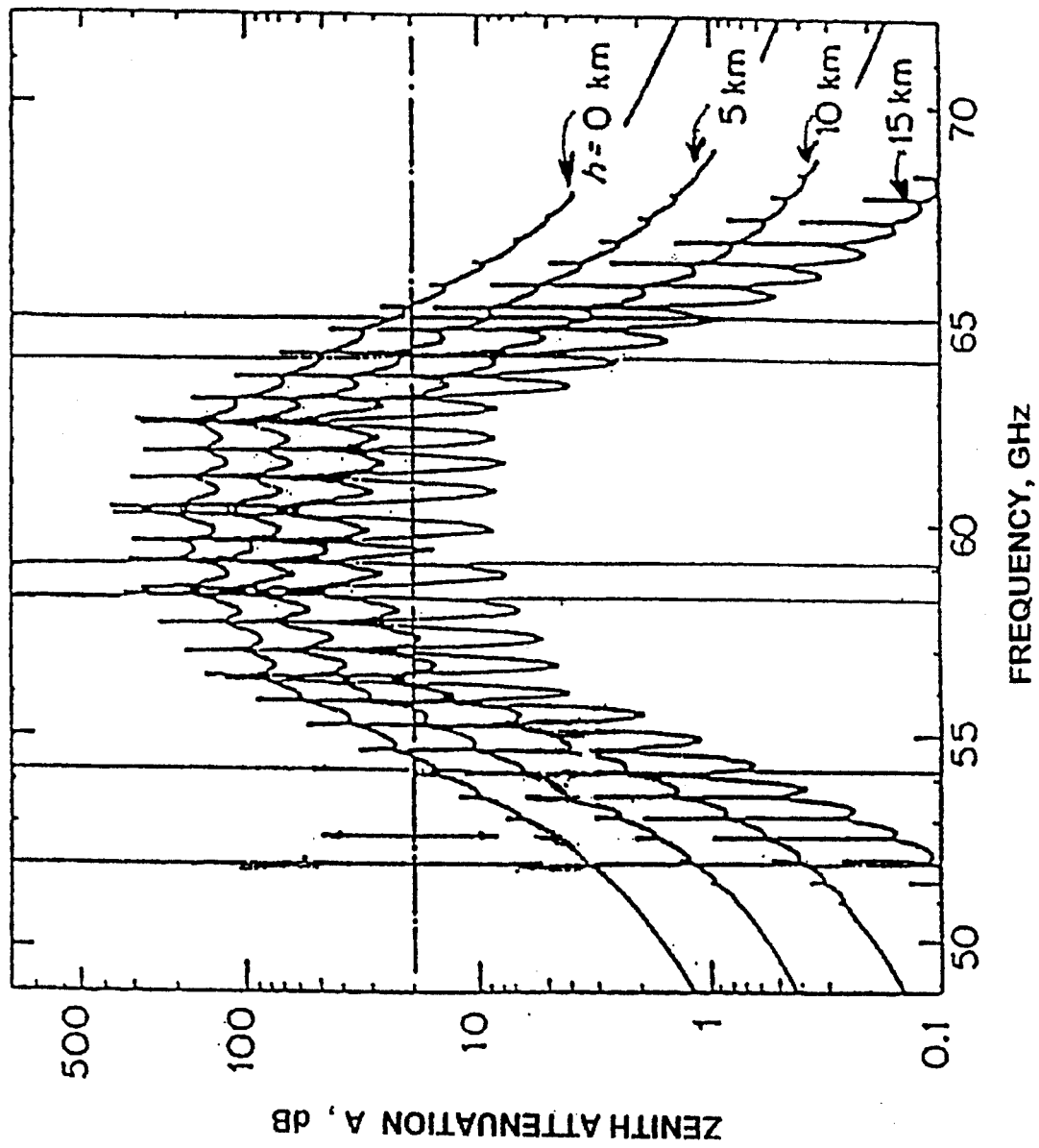
FIG. 4 is a graphic illustration of the fine structure of the 59.4 GHz oxygen line.

In its embodiment as an atmospheric temperature profiling radiometer the receiver is operated between 40 and 80 GHz to observe signal from a broad atmospheric oxygen line assemblage in this waveband. The density of atmospheric oxygen with pressure height is quite constant in time since it is a uniformly mixed gas. As shown in FIG. 4, the absorption of oxygen ranges from about 1 dB on the wing of the 59.4 GHz oxygen resonance feature (around 50 GHz) to about 100 dB at the line center (at 59.4 GHz). Because of this dependence of absorption upon frequency, and because of the predictable concentration of atmospheric oxygen, this atmospheric resonance feature is considered preferable for use in temperature profiling.

The oxygen line at 59.4 GHz is actually a superposition of a fine structure of about 40 significant lines, nearly symmetrically (but not evenly) spaced from the line center. As can be seen in FIG. 4, these fine structure lines are more apparent at high altitudes where atmospheric pressures, and therefore pressure broadening, are low.

The lines are visible at low altitude near the line center, where the quantum mechanical line strengths are high. In the wing of the resonance feature, the line strengths are down almost four orders of magnitude, while emissions are down less than two orders of magnitude from those at the line center. The result is that the fine structure features are much more prominent at the line center.

The emission at any altitude is directly proportional to the temperature of the atmosphere at the altitude. Sky brightness near the central peak of this group (near 60 GHz) is due to emissions in the lower atmosphere, and emissions at the 50 GHz wing of this band tends to originate at higher altitudes. That is, because of the high opacity of the atmosphere at frequencies near 60 GHz, the received signal originates from just in front of the antenna. As the receiver is tuned downward toward 50 GHz, the signal from higher altitudes can be resolved (up to about 10 kilometers). This results in surface observations of emissions that are weighted with altitude. By appropriately weighting observations at frequencies within the 50 to 60 GHz wave-band, and correcting for water and water vapor emissions, the temperature profile of the atmosphere can be inferred (i.e., mathematically extracted).

There are about 16 intervals in frequency between these fine structure lines between 50 and 60 GHz that are preferably used for radiometric observations. These are 50.3, 50.7, 51.25, 51.8, 52.3, 52.85, 53.3, 53.85, 54.4, 54.9, 55.45, 56.0, 56.7, 57.3, 58.0, and 58.8 GHz.

In the embodiment as a temperature profiling radiometer, downconversion mixer 51 of this receiver is driven by processor controlled tuneable frequency synthesizer 73 that is referenced to stable fixed quartz reference oscillator 75 for receiver frequency accuracy and stability. The receiver is mounted on a temperature stabilized plate for stability. The resultant receiver system is highly stable and is frequency agile across its tuning waveband. Synthesizer 73 includes tunable oscillator 77 tuned by frequency control 79 under operational control from microprocessor 71 between 13.2 to 14.7 GHz. A feed back loop between oscillator 77 and control 79 assures stability of output. Synthesizer 73 is highly stable (drift of only about one part in $10^6$ or $10^8$). The output from this synthesizer is amplified by amplifier 81 to +17 dBm and then fed to frequency quadrupler 83 and bandpass filter 85, resulting in outputs from 52.8 to 58.8 GHz. This signal is then fed into the volume of biased mixer 51, where the signal from the antenna system is downconverted.

Synthesizer 73 may be comprised of any frequency agile, stable running and continuously tunable synthesizer arrangement, such as a lumped element Gunn oscillator with PLL frequency control, a block downconverted Gunn oscillator with YIG tuned IF, varactor tuned Gunn oscillator, dielectric resonant oscillators (DROs) with frequency multiplication, an autocorrelation receiver, or a PLL YIG tuned oscillator.

Since "tipping curves" cannot be used for calibration in the 50 to 70 GHz waveband because of high atmospheric opacity, the cryogenic black body target described below is utilized for calibration of this receiver.

The reconstruction of the temperature profile from the radiometer measured radiances is based on the solution of Chandrasekhar's full radiative transfer equation for intensity at a point s along an optical path:

$$I(f, s) = I(f, 0) e^{-\int_0^s kpds'} + \int_0^s J(f, s') e^{-\int_0^s kpds''} ds'$$

where I is the intensity of the propagation, J is the intensity of the radiation source at s, f is the frequency, k is absorption coefficient, p is density of the absorbing constituent, and s is the distance along the optical path.

An effective method of retrieving temperature profiles from radiometer measurements of sky emissions is based on statistical retrieval methodology. This method consists of calculating theoretical sky emissions (called brightness temperatures) from radiosonde balloon (RAOB) soundings utilizing the oxygen line shape absorption model. Alternatively, this can be accomplished by directly measuring sky emission in selected wavebands with the radiometer concurrent with RAOB releases.

The atmospheric temperature profiles are thus known from the RAOB soundings. The sky emissions resulting from such temperature profiles are also thus known. By performing a multilinear regression fit of sky emissions in the various wavebands to the temperature profiles, a statistical relationship is established wherein the temperature at desired altitudes is determined as a function of linear dependences upon the brightnesses in each of the observed wavebands. A linear equation results for each desired altitude. The linear coefficients in these equations are called "retrieval coefficients."

Estimates of radiometer instrumental and other experimental and instrument errors can be included in the regression method to realistically constrain the solution for the temperature profile. An improved result is obtained if an average or mean temperature profile is defined from RAOB histories, and the regression is performed on the difference of temperature profiles from this mean profile, rather than the profile itself.

Other methods that are known and which could be utilized with this invention are constrained linear inversion (also known as regularization), and iterative methods wherein a first guess profile is adjusted until the calculated brightnesses match the measured brightnesses.

Tunable frequency synthesizer 73 offers extreme frequency control and fast tuning. The tunable local oscillator enables more versatility of the radiometer in that an ensemble of frequencies can be software selected by a user to suit the immediate requirement of the radiometer. For example, a requirement for a more resolute temperature profile would dictate more frequencies to be selected, while rapid instrument cycle times would dictate fewer frequencies. A humid climate would benefit from an additional observation frequency in the 52 to 54 GHz range. Thus, frequency agility has significant benefits over historically used fixed oscillators.

The frequency agility of frequency synthesizer 73 allows this receiver to emulate other radiometers, as the frequency set of other radiometers can be software selected. Direct comparison, and/or transfer of calibration, are therefore possible with this radiometer.

A principal advantage of this invention is that it is software tunable in frequency. This allows user choice and changes in the number and location of receiver channels. Data is recorded for post-process (and real-time) profile retrieval with any number of software retrieval algorithms.

Figure 5:
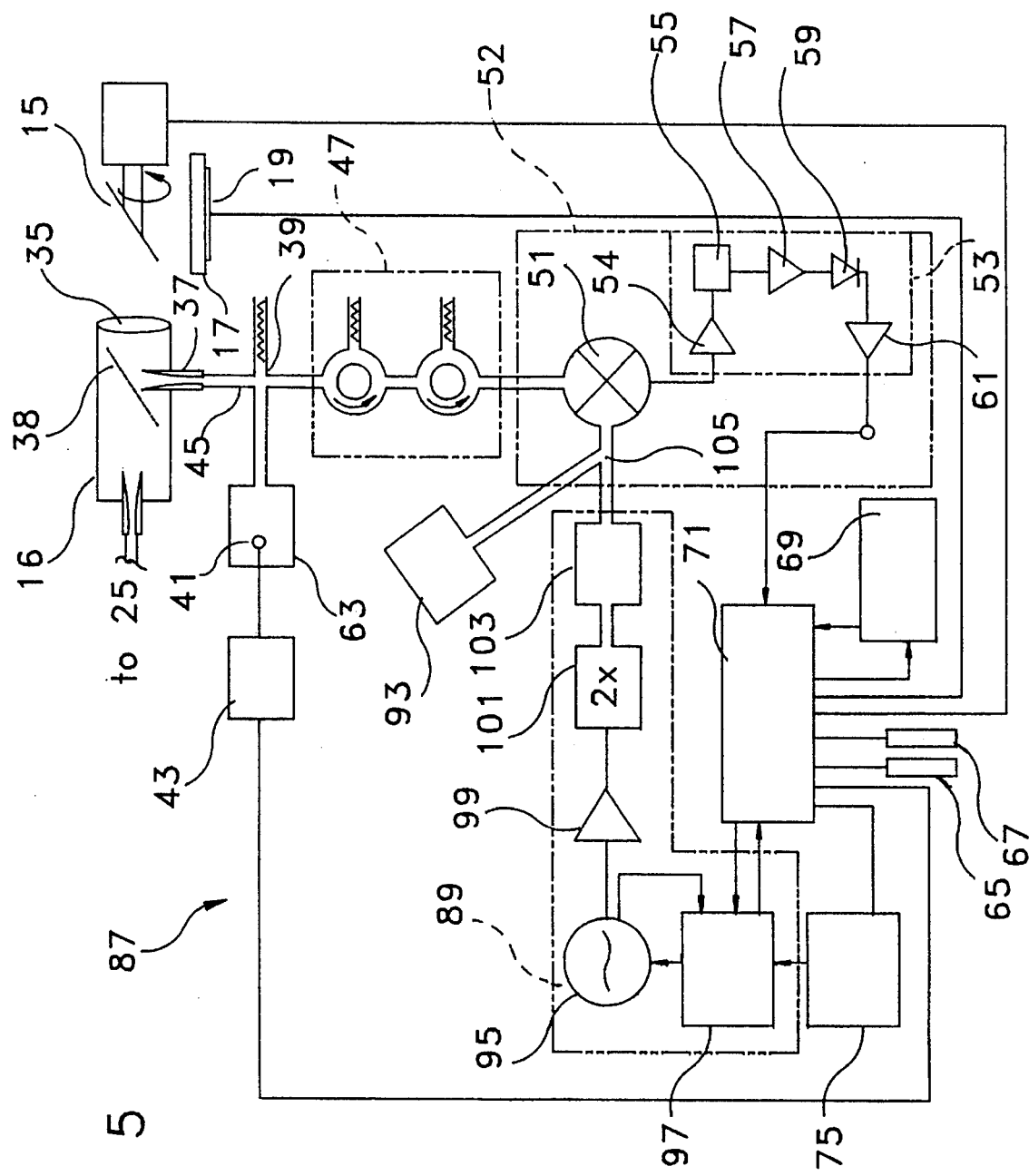
FIG. 5 is a diagrammatic illustration of the water vapor profiling apparatus in accord with this invention.

In its embodiment as an atmospheric water vapor profiling radiometer shown in FIG. 5, the receiver is operated in the K and Ka bands using WR34 waveguide hardware as is described in U.S. Pat. No. 4,873,481. As taught therein, one receiving frequency is between about 30 and 36 GHz (preferably at 31.4 GHz) to enable measurement of cloud liquid water. In water vapor profiler 87, however, the other receiving channel replaced with a frequency synthesizer 89 capable of tuning across the atmospheric water vapor emission resonance line that is centered at 22.235 GHz. This tuning capability is accommodated with waveguide launcher to inject a signal from stable tuneable synthesizer 89 into mixer 51.

While a receiver for tuning across the 22.235 GHz water vapor line is discussed herein, it should be realized that other frequency regimes could be used, for example using a tunable frequency synthesizer to tune across the 183 GHz water vapor line, to accomplish the benefits of this invention.

Figure 6:
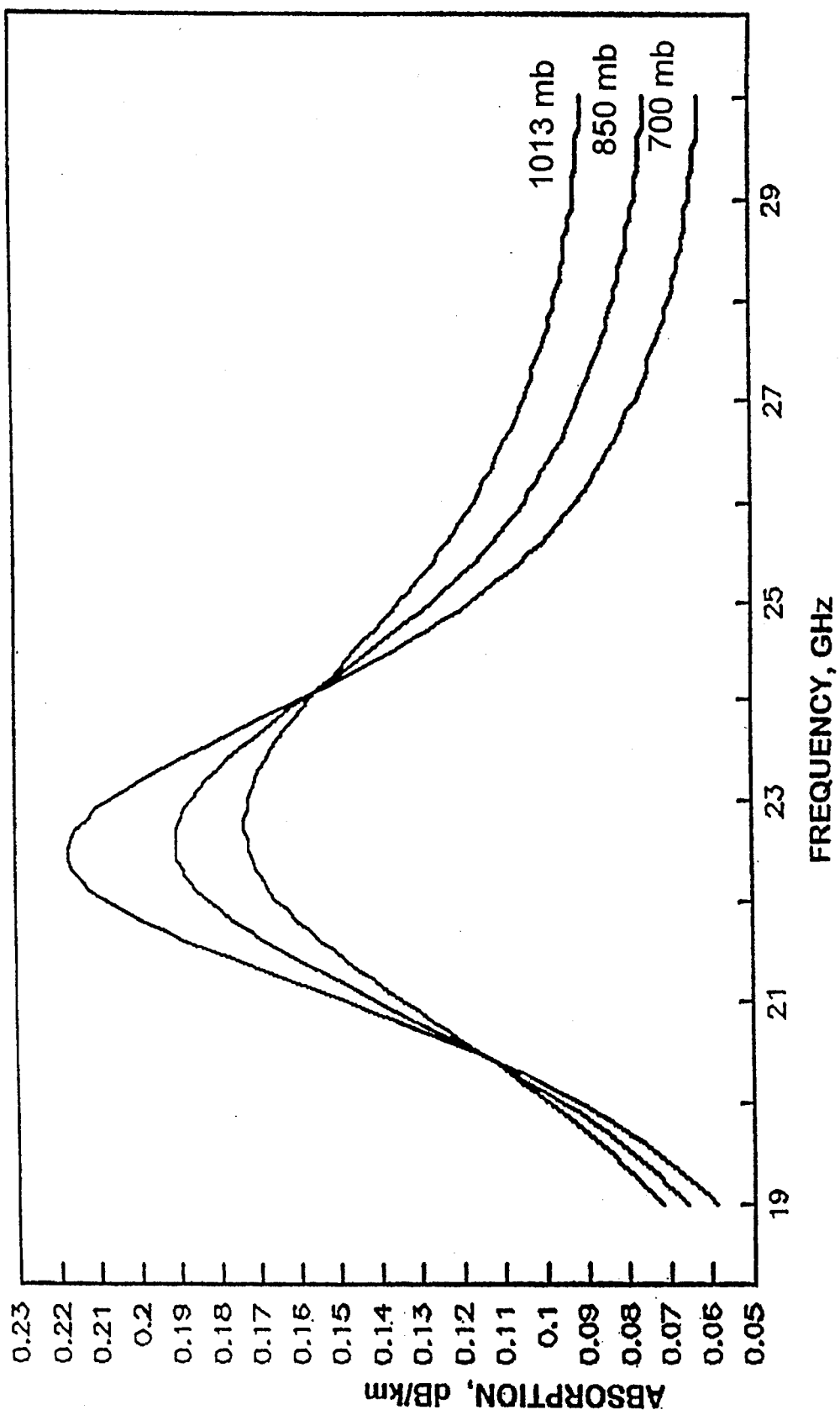
FIG. 6 is a graphic illustration of the pressure broadening phenomena centered at the 22,235 GHz water vapor line.

As shown in FIG. 6 (illustrating pressure broadening in a 50% RH and +15C atmosphere at 1013 mb, 850 mb and 700 mb of altitude for the 22 water vapor line), because the 22.235 GHz line is pressure broadened, the width of this line contains information on the altitude of the emitting water vapor. Water vapor at high altitudes, and therefore low pressure, emits in a narrow line, very close to the line center; water vapor at low altitude is pressure broadened and therefore emits significant signal away from the line center. By making a series of observations from about 16 to 28 GHz, one can utilize this line broadening to determine the density of water vapor as a function of altitude.

As shown in FIG. 5, 31.4 Gunn diode oscillator 93 is fed to mixer 51. The output and frequency of oscillator 93 are stabilized by stabilizing the physical temperature of the oscillator. To minimize the settling time of the Gunn oscillator by simmering the diode junction, 1.1 volts is maintained on the diode when not being driven by the 6 volt operating voltage. 22 to 25 GHz synthesizer 89 (including variable oscillator 95 tunable by frequency control 97 under commands from microprocessor 71 between about 11 and 12.5 GHz, amplifier 99, frequency doubler 101 and band pass filter 103) alternates in function with the 31.4 GHz channel, and tunes to each of an ensemble of user-defined frequencies that are entered into a configuration file in computer 69. Oscillator 93 and synthesizer 89 are alternately fed into a mixer 51 via waveguide combiner 105. Sky measurement routines are user-defined in a procedure file stored in computer 69.

The calibration of this instrument involves determining the level of signal injected by noise diode 43, and can be accomplished by observing blackbody targets of two different known temperatures. This output differential is compared with the signal that the noise diode contributes, thereby calibrating the noise diode. One method of utilizing such target calibrations is to use the sky as one target, and ambient blackbody 17 as the other. This is called the "tipping curve" method, and is described in the U.S. Patent cited above. A second method of calibration is to implement the cryogenic blackbody target that is described below.

Downconversion is direct with synthesizer 89 at the desired resonance line frequency. The sample width is determined by the bandwidth of filter 55, for instance 5 to 30 MHz. Both the upper and lower sidebands would be included. This method give a total edge-to-edge sample bandwidth of 60 MHz, but only 50 MHz passes the filter. The central 10 MHz is not sampled; this is necessary to eliminate the phase noise of the oscillators. The advantage to this dual-sideband method is simplicity and low cost. Single-sideband methods could of course be utilized.

For data conversion, all algorithms relating atmospheric parameters to microwave observables are based on the equation of radiative transfer in the Rayleigh-Jeans approximation. For a non-scattering atmosphere, the microwave brightness temperature measured by a ground-based radiometer is determined by the atmospheric profiles of temperature and absorption:

$$T_B = \int_0^\infty T(s)k(s) e^{-\int_0^s k(s')ds'} ds + T_c e^{-\int_0^\infty k(s)ds} \quad (1)$$

where $T_B$=the frequency dependent brightness temperature (K), $T(s)$=the atmospheric temperature along the direction of s, $k(s)$=the atmospheric absorption at s, dependent on temperature, pressure, water vapor and liquid density, and $T_C$=the cosmic background temperature impinging at the top of the atmosphere.

Development of an algorithm for retrieving any of the atmospheric parameters which constrain measured brightness temperatures requires a method for inverting the equation:

$$\alpha(v, z) = \frac{S}{\pi} \left(\frac{v}{v_0}\right)^2 \left[ \frac{\gamma(z)}{(v - v_0)^2 + \gamma^2(z)} + \frac{\gamma(z)}{(v + v_0)^2 + \gamma^2(z)} \right] \quad (2)$$

Where S is the line strength parameter and $\gamma(z)$ is the line width parameter.

The accuracy of the retrieval algorithm depends on the selection of microwave and other available observables, observable accuracies, and the accuracies of our models which relate the integrand properties of equation (1) to the desired retrieved parameters (in this case vapor density vs. altitude).

At least three different techniques could be used. Statistical retrievals utilize a priori correlations of the observables with the desired atmospheric parameters. The correlations are obtained either experimentally, in which observables are measured at times when independent determinations of the atmospheric parameters are available, or computationally, in which model dependent observables are calculated (equation 1) from a data base of atmospheric conditions, usually radiosondes. Linear retrieval coefficients are obtained from the complete data archive by multi-linear regression, taking into account the noise characteristics of the observables.

For the task of vapor profiling, the statistical method is generally most applicable to measurement systems in which the number of independent observables is significantly less than the number of discrete altitude vapor densities desired. However, the formulation is straightforward and well established.

The method of direct linearized inversion reduces equation (1) to a matrix equation by approximating the integrand as a weighting function times the actual vapor profile and then reducing the integral to numerical quadrature. The weighting functions are obtained by a first order Taylor expansion of the true non-linear relationship about some a priori estimate of the true profile of atmospheric properties. The biases produced by the a priori estimate can be reduced by iterations in which the weighting functions are recomputed for each new vapor profile solution. The inversion solutions can also be further constrained by adding ground truth measurements to the microwave observables using the method of Lagrange multipliers.

The method of maximum probability employs a search technique to determine the desired atmospheric parameters which maximize a product function dependent of the differences between measured and computed (equation 1) observables. Each observable is assumed to be characterized by specified Gaussian noise. For each candidate atmosphere "solution" to the inversion of equation (1), theoretical observables are computed and compared to the measurements by computing the Gaussian function value from the "measured" minus "computed" difference. The product of all such observable "probabilities" constitutes a measure of the appropriateness of the candidate atmospheric profile solution.

The final solution is found by determining the atmospheric profile which maximizes this function. For the case of vapor profiling, solutions are constrained by designating a priori bounds on the height-dependent variability of the vapor density, usually determined from radiosonde statistics. To allow for anomalous, but physically realizable solutions, the allowable bounds of variability can be expanded. The solution search is stabilized by imposing correlation constraints on the candidate vapor density profiles. The maximum probability method has the advantage of incorporating the actual non-linearities inherent in equation (1) into the solution search.

For vapor profiling, the accuracies of all of the above techniques depend on the accuracy of the vapor absorption model near the 22.2 GHz resonance. Recent work has improved the absorption model constraints utilized, and the new models can be incorporated into software as they are developed.

Figure 7:
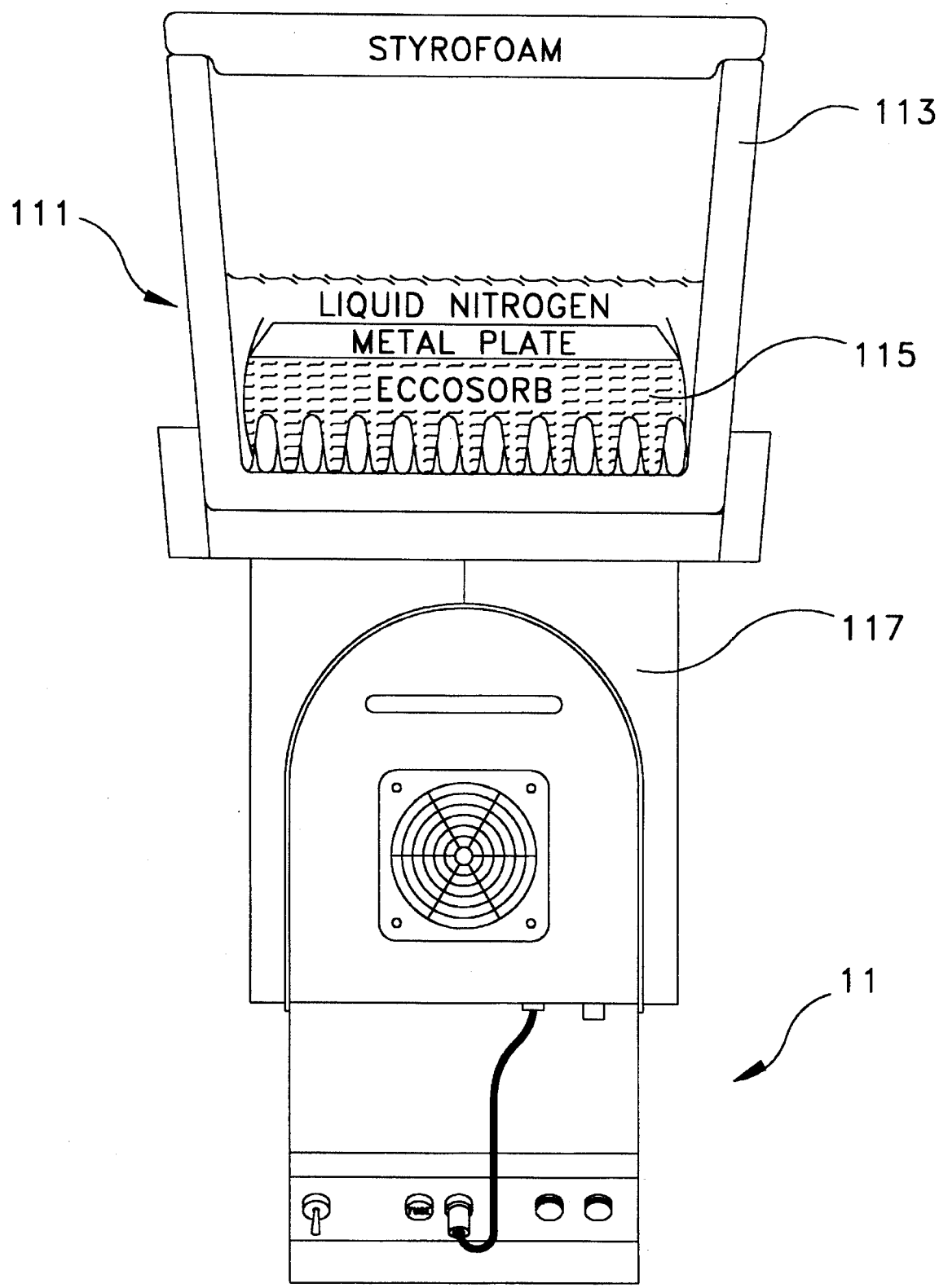
FIG. 7 is a sectional illustration of the cryogenic black body calibration target of this invention mounted on the apparatus of this invention.

Turning now to FIG. 7, cryogenic blackbody target 111 includes polystyrene foam container 113 into which opencell convoluted black body foam 115 is placed. This foam is immersed in liquid nitrogen. Measuring the temperature of the liquid nitrogen, and therefore of the black body, to better than several tenths of a degree would be very difficult with thermometer devices. However, the liquid nitrogen reaches an equilibrium temperature that varies slightly with atmospheric pressure, but can be known to within several hundredths of a degree with a barometric pressure measurement. The liquid nitrogen temperature, and therefore the target temperature in Kelvins can be expressed as:

$$LN2\ T(K) = 68.23 + 0/009037 \times P(\text{millibars})$$

Container 113 is a very low loss dielectric and is therefore transparent to microwave radiation. The radiometer instrument can therefore look through the polystyrene foam at the black body and thereby measure the signal from a target of precisely known temperature.

To calibrate radiometer instrument 11, saddle 117 supporting polystyrene container 113 is placed on top of the radiometer. Liquid nitrogen is introduced into the container, and the cryogenic target is placed in the saddle. The radiometer is commanded to observe the cryogenic target and the ambient blackbody target (17 in FIG. 1) in succession. The difference in video volts with noise diode 41 off and on is then measured, and this measurement converted to temperature by multiplying by the above quotient. Thus the cryogenic target calibration is transferred to the noise diode for long term diode use. This procedure is repeated for all receiver frequencies, and entered into the calibration log file in computer 69.

Other cryogenic liquids with different boiling point temperatures can be used to produce a variety of calibration points. Reflective metal blinders (i.e., the internal walls of saddle 117) are used to ensure that the entire field of view of the radiometer (including side lobes) is terminated into the blackbody target, minimizing calibration errors. Dew blower 33 of the radiometer avoids condensation of water on the under side of the polystyrene foam container.

The insertion loss, and therefore the temperature contribution, of container 113 is determined as follows. The radiometer instrument is pointed to a stable cold target such as a second liquid nitrogen blackbody target. The polystyrene container is put into the radiometer beam and the increase in voltage is noted. This voltage increase is the contribution of the polystyrene, and is proportional to the difference between the liquid nitrogen cold target implemented and ambient. One inch of 1.5 lb/cubic foot polystyrene foam will contribute approximately 0.01655K per K difference between the Styrofoam and the cold target at 23 GHz, 0.02190K per K at 31 GHz, and 0.03836K per K at 55 GHz. This correction scales as the thickness of the foam in wavelengths.

A slight correction is also made for the reflection from the lower surface of the liquid nitrogen that is against the bottom of the Styrofoam container. This correction is independent of wavelength, and is 0.00724K per K. This correction is typically about 1.5K.

Figure 8:
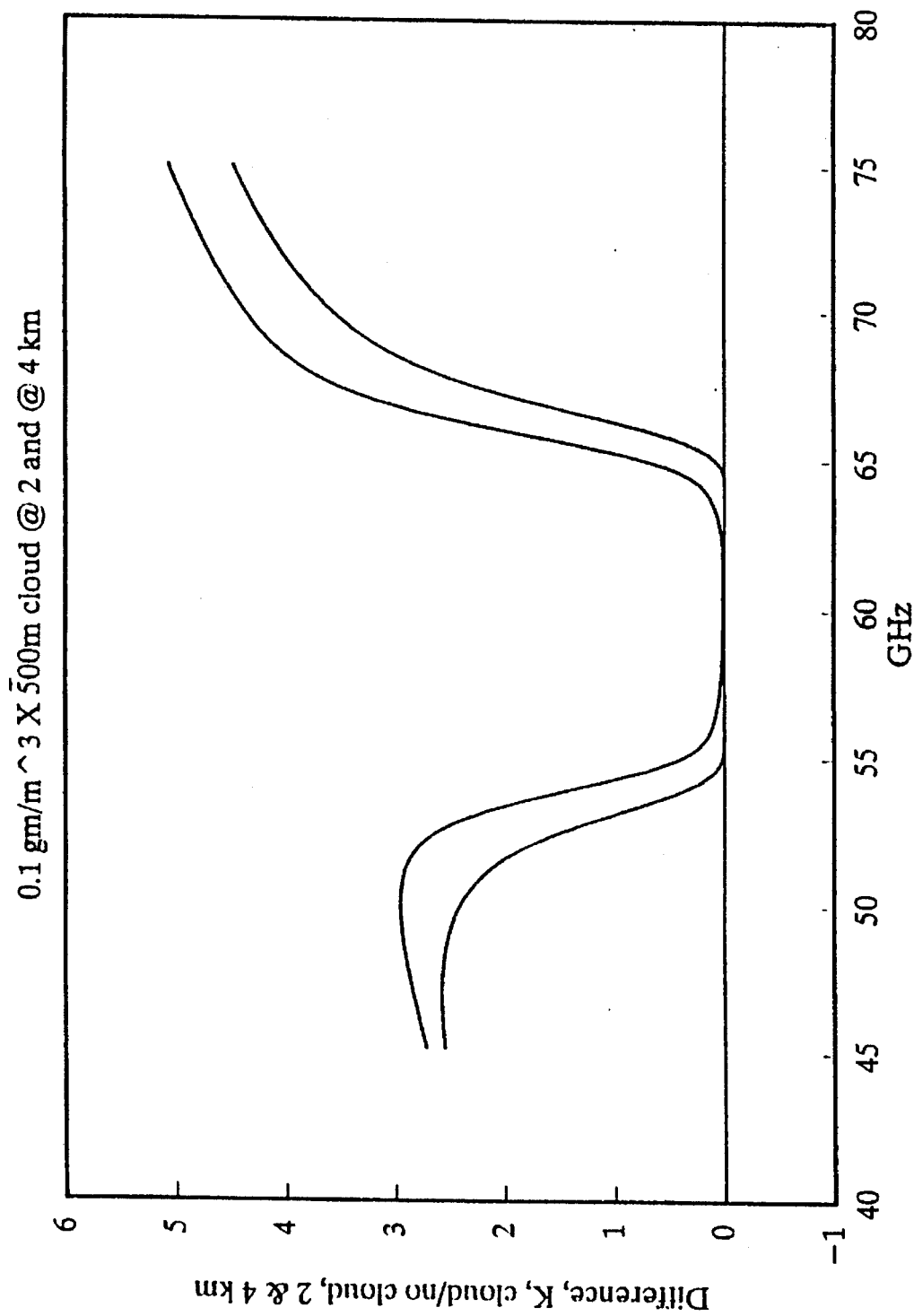
FIG. 8 is a graphic illustration showing the difference in brightness temperature that is observed using the invention as illustrated in FIG. 8.

In the embodiment of this invention used as a cloud liquid water vapor profiler as shown in schematic form in FIG. 8, the receiver is operated in both the U and E wavebands in a simultaneous manner. The radiometer receiver can be two separate receivers as in FIG. 3 (operating under the control of a single processor unit 69), one for operation in each of the wavebands, or can be a single receiver that can tune across both wavebands. In the case of dual receivers, the receiver components, operation and calibration are the same as the components, operation and calibration of the temperature profiling receiver above discussed.

By making a series of observations on each side of the atmospheric oxygen feature centered at 60 GHz from about 50 to 60 and about 60 to 70 GHz, one can determine the cloud liquid content as a function of height above the antenna.

While the atmospheric oxygen resonance at 60 GHz is discussed herein, other atmospheric resonances could be utilized, such as water vapor resonances or the oxygen resonance at 118.75 GHz.

Atmospheric temperature profiling may be accomplished by observing frequencies on either the low frequency side between 40 and 60 GHz, or on the high frequency side of the line between 60 and 80 GHz. In a steady state, cloud liquid emits approximately as it absorbs. The absorption of liquid water is given by:

$$\alpha(dB/km) = \frac{0.819 \rho_{liquid}}{\epsilon''(y^2 - 1)} f$$

where f is the frequency of observation, Pliquid is the cloud liquid density in g/m³ and $\epsilon''$ is the imaginary part of the refractivity for water, and where:

$$y = \frac{\epsilon' + 2}{\epsilon''}$$

and:

-continued $$\epsilon' = \frac{f}{f_p} \frac{\epsilon_0 - \epsilon_1}{1 + (f/f_p)^2} + \frac{f}{f_s} \frac{\epsilon_1 - \epsilon_2}{1 + (f/f_s)^2} + \epsilon_2$$

and:

$$\epsilon'' = \frac{\epsilon_0 - \epsilon_1}{1 + (f/f_p)^2} + \frac{\epsilon_1 - \epsilon_2}{1 + (f/f_s)^2}$$

The three permittivity constants are:

$$\epsilon_0 = 77.66 + 103.3 \left( \frac{300}{T(K)} - 1 \right)$$

$$\epsilon_1 = 5.48$$

$$\epsilon_2 = 3.51$$

The relaxation frequencies are:

$$f_p = 20.09 - 142.4 \left( \frac{300}{T(K)} - 1 \right) + 294 \left( \frac{300}{T(K)} - 1 \right)^2$$

$$f_s = 590 - 1500 \left( \frac{300}{T(k)} - 1 \right)$$

Cloud liquid water emits in the microwave region approximately as the square of the frequency, and therefore contributes more signal at frequencies on the high frequency side of the oxygen line than on the low frequency side. This asymmetric contribution to frequencies across the oxygen line results in a skew in the oxygen line shape profile relative to the oxygen line shape profile that is observed in the absence of cloud liquid. Further, the atmosphere is rather opaque near the oxygen line center, while becoming more transparent as frequencies more distant from the line center are tuned by the synthesizer and observed. Therefore, skew in the signal from opposite sides of the 60 GHz line near the line center at, say, 58 and 62 GHz, is due to cloud liquid near the radiometer antenna. Conversely, skew in signal from opposite sides of the oxygen line more removed from the line center at, say, 50 and 70 GHz, is due primarily to cloud liquid at higher altitude. By tuning the synthesizer, thereby scanning from the line center out onto the line wings at higher and lower frequencies, altitude information on cloud liquid is obtained. Temperature profile information, corrected for the cloud liquid contribution, can be simultaneously obtained.

FIG. 8 shows the difference in brightness temperature that would be observed across the liquid profiling wavebands using a vertically staring antenna at sea level. These two cases present the additional signal that would be observed, above the cloudless atmosphere signal, for a cloud containing 0.2 grams per cubic meter of liquid water with a thickness of 250 meters at an altitude of 2 kilometers above the antenna and at an altitude of 4 kilometers above the antenna. The skew in the liquid contribution is apparent, as is the dependence of the signal upon altitude of the liquid water.

As may be appreciated from the foregoing, an improved temperature profiling radiometer and a water vapor profiling radiometer have been provided which does not utilize multiple oscillators to achieve the profile thus simplifying the design, making the radiometer both lighter and less costly, and reducing power requirements. Additionally, there is essentially no local oscillator warm-up time required.

There are no electromechanical or Dicke switches utilized to add to the receiver noise and hence temperature, and therefore diminish the receiver sensitivity. The overall radiometer 11 weighs less than 35 kg and consumes about 150 watts maximum (in cold ambient temperatures). The volume and shape are about two cubic feet, 27"×18"×9".

What is claimed is:

1. For use in a passive remote sensing device having antenna means for receiving atmospheric microwave emissions containing frequencies of interest, an apparatus for providing a profile of a selected atmospheric characteristic comprising:

continuously tunable oscillating means for providing a plurality of selected frequency outputs; and downconverting means for receiving said plurality of selected frequency outputs from said oscillating means and said emissions from said antenna means and, responsive thereto, providing output signals indicative of microwave energy emitted by the atmosphere at said frequencies of interest and representing said profile of said atmospheric characteristic.

2. The apparatus of claim 1 wherein said received frequencies of interest are a broad atmospheric oxygen line assemblage in a waveband between about 50 and 60 GHz, and wherein said oscillating means is tunable across said waveband to thereby provide said output signals from said downconverting means representing a profile of atmospheric temperature.

3. The apparatus of claim 2 wherein said plurality of selected frequency outputs are any selected ones of about 16 frequency intervals between about 50 and 60 GHz.

4. The apparatus of claim 1 wherein said received frequencies of interest are a pressure broadened water vapor line in a selected waveband, and wherein said oscillating means is tunable across said waveband to thereby provide said output signals from said downconverting means representing an altitude profile of atmospheric water vapor.

5. The apparatus of claim 4 wherein said pressure broadened water vapor line waveband is in the range of about 16 to 28 GHz, and wherein said received frequencies of interest also include a frequency in a waveband in the range of 30 to 36 GHz, said apparatus further comprising means for resolving said emissions in said 30 to 36 GHz range at said downconverting means to provide an output signal indicative of liquid content of the atmosphere.

6. The apparatus of claim 1 wherein said oscillating means includes a crystal-referenced, highly stable tunable oscillator connected with said downconverting means and frequency control means connected with said tunable oscillator for controlling selection of said plurality of frequencies.

7. The apparatus of claim 6 wherein said downconverting means includes mixing means for receiving said emissions and said selected frequency outputs and providing said output signals that selectively represent atmospheric microwave power emitted at different frequency components of said profile.

8. The apparatus of claim 1 further comprising a controller for operating the device, storing said output signals, and controlling tuning of said oscillating means to each of an ensemble of user defined frequencies.

9. A passive microwave radiometer for determining a profile of a selected atmospheric characteristic comprising:

antenna means for receiving atmospheric microwave emissions containing frequencies of interest;

frequency synthesizing means tunable across a plurality of user selected frequency intervals that are responsive to said atmospheric microwave emissions at said frequencies of interest; and downconverting means connected with said antenna means and said frequency synthesizing means for generating output signals indicative of said atmospheric microwave emissions at said frequencies of interest responsive to receipt of said emissions and tuning of said frequency synthesizing means across said intervals to provide said profile.

10. The radiometer of claim 9 further comprising means for characterizing gain and offset of said radiometer at each observation to enhance accuracy of said output signals and thus said profile.

11. The radiometer of claim 9 further comprising processor means for automatically controlling tuning of said frequency synthesizing means to each of an ensemble of user defined frequencies.

12. The radiometer of claim 9 wherein said frequency synthesizing means includes a tunable oscillator connected with a frequency controller referenced to a stable frequency reference.

13. The radiometer of claim 9 wherein the atmospheric characteristic is atmospheric temperature and wherein said frequency synthesizing means is tunable across selected intervals between 40 and 80 GHz.

14. The radiometer of claim 9 wherein the atmospheric characteristic is water vapor content, and wherein said frequency synthesizing means is tunable across selected intervals over about 6 GHz in a band responsive to said frequencies of interest corresponding to a selected pressure broadened water vapor line.

15. The radiometer of claim 9 wherein the atmospheric characteristic is cloud liquid water content, and wherein said frequency synthesizing means is tunable across separate wavebands at the low and high frequency sides of either of a selected water vapor or oxygen resonance line.

16. The radiometer of claim 15 wherein said selected water vapor or oxygen resonance line is an oxygen resonance at 60 GHz, said frequency synthesizing means being tunable between about 40 and 60 GHz at said low frequency side and between about 60 and 80 GHz at said high frequency side.

17. The radiometer of claim 9 further comprising calibration means for calibrating said radiometer, said calibration means including a cryogenic target and mounting means for removably positioning said cryogenic target above said antenna.

18. A method for profiling a selected atmospheric characteristic comprising the steps of:

admitting atmospheric microwave emissions containing frequencies of interest into a volume;

synthesizing a plurality of signals responsive to said atmospheric microwave emissions at said frequencies of interest and admitting said signals into said volume to downconvert said emissions from said frequencies of interest; and generating output signals indicative of microwave energy emitted by the atmosphere at said frequencies of interest to provide a profile of said atmospheric characteristic.

19. The method of claim 18 wherein said atmospheric characteristic is atmospheric temperature, wherein said frequencies of interest are a broad band atmospheric oxygen line assemblage in a waveband between about 40 and 80 GHz, and wherein the step of synthesizing a plurality of signals includes tuning across said waveband to downconvert said emissions at said frequencies of interest.

20. The method of claim 18 wherein said atmospheric characteristic is atmospheric water vapor content, wherein said frequencies of interest are a pressure broadened water vapor line in a selected waveband, and wherein the step of synthesizing a plurality of signals includes tuning across said waveband to downconvert said emissions at said frequencies of interest.

21. The method of claim 20 wherein said pressure broadened water vapor line waveband is in the range of about 16 to 28 GHz.

22. The method of claim 20 wherein said atmospheric characteristic is also atmospheric liquid content, and wherein said frequencies of interest also include a frequency in the range of about 30 to 36 GHz, said method further comprising the step of providing a signal to downconvert said emissions at said 30 to 36 GHz frequency of interest.

23. The method of claim 18 further comprising the steps of repeatedly admitting emissions, synthesizing responsive signals and generating output signals to provide ongoing observations, and characterizing error producing environmental conditions at each said observation to reduce error in said output signals and thus in said profile.

24. The method of claim 18 wherein the step of synthesizing signals includes tuning a crystal referenced, highly stable oscillator to each frequency of a user selected ensemble of frequencies.

25. The method of claim 18 wherein the atmospheric characteristic is cloud liquid water content, and wherein said frequencies of interest are assemblages in separate wavebands at the low and high frequency sides of either of a selected water vapor or oxygen resonance line, and wherein the step of synthesizing a plurality of signals includes simultaneously tuning across said wavebands to downconvert said emissions at said frequencies of interest.

26. The radiometer of claim 25 wherein said selected water vapor or oxygen resonance line is an oxygen resonance at 60 GHz, said low frequency side being between about 40 and 60 GHz and said high frequency side being between about 60 and 80 GHz.

* * * * *